(12) United States Patent
Castracane et al.

(10) Patent No.: US 10,117,990 B2
(45) Date of Patent: Nov. 6, 2018

(54) MICROFLUIDIC INTRAVITAL WINDOW

(71) Applicants: THE RESEARCH FOUNDATION FOR THE STATE UNIVERSITY OF NEW YORK, Albany, NY (US); ALBERT EINSTEIN COLLEGE OF MEDICINE, INC., Bronx, NY (US)

(72) Inventors: James Castracane, Albany, NY (US); Logan Butt, Albany, NY (US); David Entenberg, Granite Springs, NY (US); Lauren Sfakis, Albany, NY (US); John Condeelis, Bronx, NY (US)

(73) Assignees: The Research Foundation for the State University of New York, Albany, NY (US); Albert Einstein College of Medicine, Inc., Bronx, NY (US)

( * ) Notice: Subject to any disclaimer, the term of this patent is extended or adjusted under 35 U.S.C. 154(b) by 155 days.

(21) Appl. No.: 15/371,493

(22) Filed: Dec. 7, 2016

(65) Prior Publication Data

US 2018/0154073 A1    Jun. 7, 2018

(51) Int. Cl.
*A61M 31/00*    (2006.01)
*A61M 5/142*    (2006.01)
(Continued)

(52) U.S. Cl.
CPC ... *A61M 5/14276* (2013.01); *A61B 5/150007* (2013.01); *A61B 17/0218* (2013.01);
(Continued)

(58) Field of Classification Search
CPC .. A61M 2037/0023; A61M 2039/2493; A61M 37/0015; A61M 39/24; A61M 5/14276; A61M 5/172
See application file for complete search history.

(56) References Cited

U.S. PATENT DOCUMENTS

2004/0151666 A1    8/2004    Dewhirst et al.
2009/0185980 A1*   7/2009    Dong ................. G02B 21/0076
                                                                 424/9.2
(Continued)

OTHER PUBLICATIONS

Wright et al., On-Chip Open Microfluidic Devices for Chemotaxis Studies, Microsc Microanal., Aug. 2012; 18(4), 12 pages.
(Continued)

*Primary Examiner* — Rebecca E Eisenberg
(74) *Attorney, Agent, or Firm* — Heslin Rothenberg Farley & Mesiti P.C.

(57) ABSTRACT

A microfluidic intravital window includes an intravital imaging window adapted for implantation adjacent target tissue of a live animal, and a microfluidic fluid source and delivery system physically integrated into the window for controlled delivery of fluids to target tissue via the window. The microfluidic fluid source and delivery system is self-contained and completely located within the intravital imaging window, and includes at least one preloaded fluid reservoir, at least one fluid port in fluidic communication with both the at least one preloaded fluid reservoir and the target tissue, and at least one light activated fluid flow control device situated between the at least one preloaded fluid reservoir and at least one fluid port, to facilitate simultaneous in vivo viewing and remotely controlled fluid delivery to the target tissue.

21 Claims, 17 Drawing Sheets

(51) Int. Cl.
*A61M 5/172* (2006.01)
*A61M 39/24* (2006.01)
*A61B 17/02* (2006.01)
*A61M 37/00* (2006.01)
*A61D 1/00* (2006.01)
*A61B 5/15* (2006.01)

(52) U.S. Cl.
CPC .............. *A61D 1/00* (2013.01); *A61M 5/172* (2013.01); *A61M 37/0015* (2013.01); *A61M 39/24* (2013.01); *A61M 2037/0023* (2013.01); *A61M 2039/2493* (2013.01)

(56) References Cited

U.S. PATENT DOCUMENTS

2014/0121493 A1* 5/2014 Shi .......................... A61D 3/00
600/411

2014/0308207 A1 10/2014 Janetopoulos et al.

OTHER PUBLICATIONS

He, et al., In vivo quantitation of rare circulating tumor cells by multiphoton intravital flow cymometry, Proc Natl Acad Sci USA, Jul. 10, 2007, 104(28), pp. 11760-11765.
Choi, et al., Intravital Microscopic Interrogation of Peripheral Taste Sensation, Scientific Reports 5, 2015, 6 pages.
Bucolo, et al., A Disposable Micro-Electro-Optical Interface for Flow Monitoring in Bio-Microfluidics, Twelfth International Conference on Miniaturized Systems for Chemistry and Life Sciences, 2008, pp. 1579-1580.
Myneni, et al., Intravital Microfluidic Windows for Delivery of Chemicals, Drugs and Probes, Microsc. Microanal, 20 (Suppl 3), 2014, pp. 1352-1353.

* cited by examiner

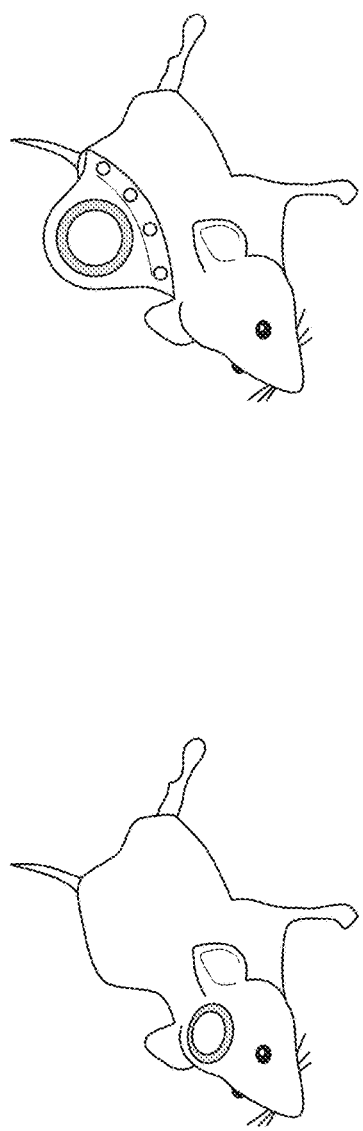
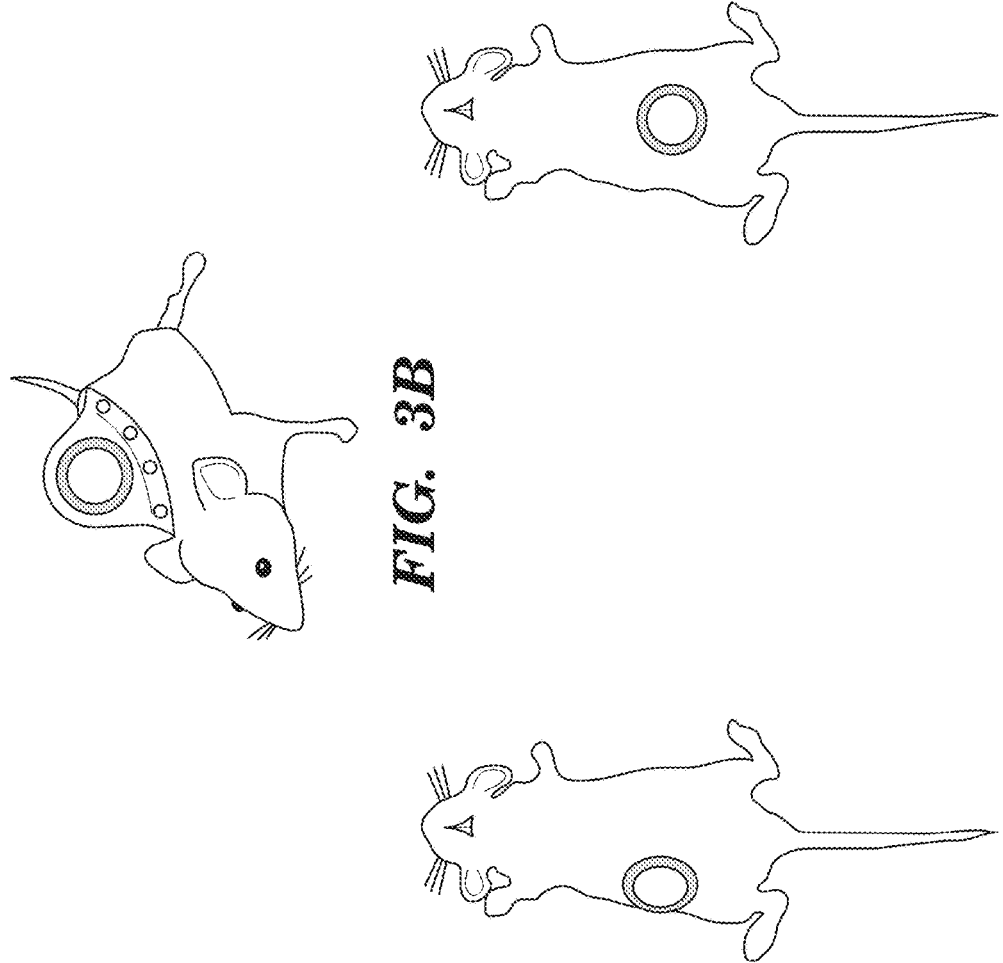
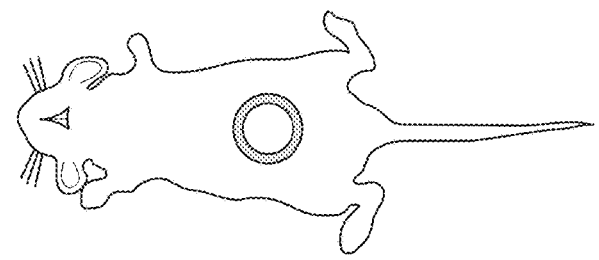
FIG. 3A
FIG. 3B
FIG. 3C
FIG. 3D

STEP A: CLEAN SILICON WAFER 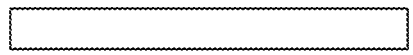
STEP B: SPIN, BAKE SU-8 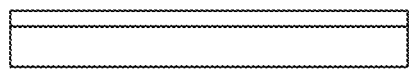
STEP C: EXPOSE, BAKE SU-8 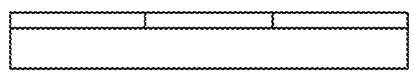
STEP D: REPEAT STEPS B+C FOR SECOND SU-8 LAYER 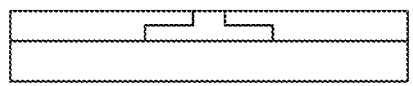
STEP E: DEVELOP SU-8 
STEP F: POUR/SPIN PDMS 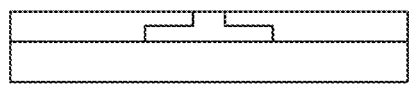
STEP G: REMOVE PDMS 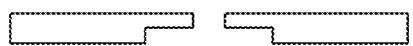
STEP H: SEAL PDMS TO GLASS 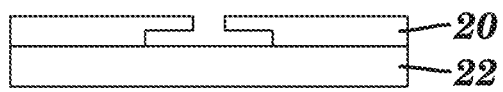
*FIG. 5*

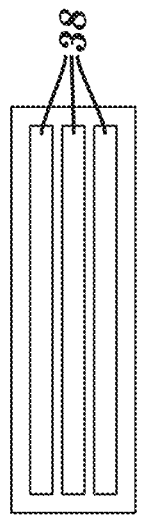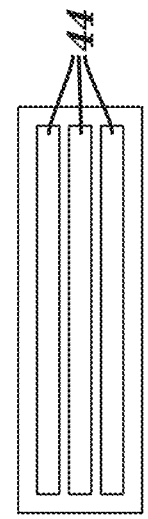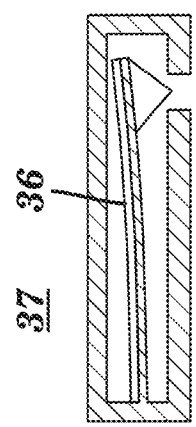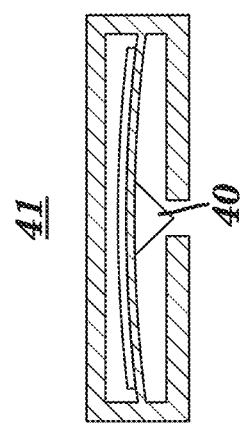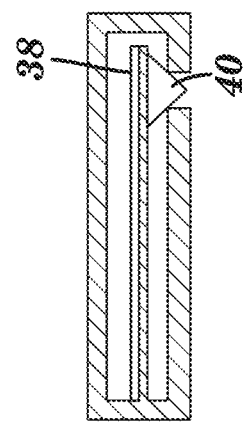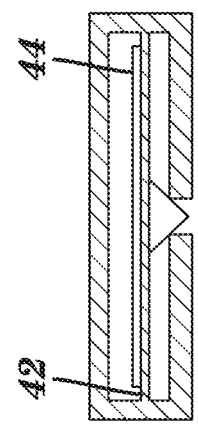

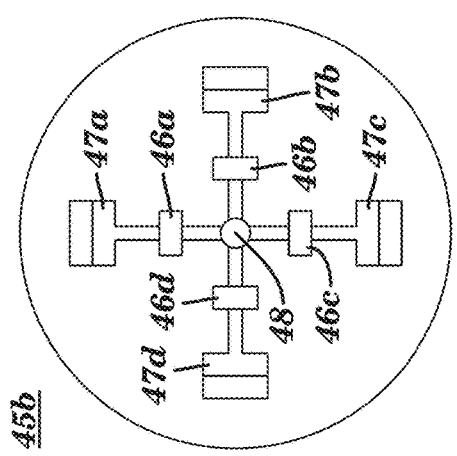
FIG. 13

MICROFLUIDIC INTRAVITAL WINDOW

GOVERNMENT RIGHTS STATEMENT

This invention was made with government support under grant/contract number U54-CA126511-01 awarded by The National Institute of Health. The government has certain rights in the invention.

FIELD OF THE INVENTION

The present invention relates, generally, to devices for in vivo viewing of target tissue, and, more particularly, to a microfluidic intravital window which provides both high-resolution in vivo imaging over extended time periods and remotely controlled release of fluids into the target tissue, e.g., controlled release of factors into a tumor microenvironment.

BACKGROUND ART

With more than 1.2 million cases diagnosed each year, breast cancer is the most common malignancy in women resulting in approximately 500,000 deaths per year worldwide with 90% of these deaths due to metastasis. While advances in gene expression profiling of primary tumor cells have recently led to new tools with some prognostic power for recurrence, there are few predictors of actual metastatic risk. After more than 10 year of investigation into the tumor microenvironment (epitomized by the Tumor Microenvironment Network program at the National Cancer Institute) it is becoming increasingly clear that, in addition to driven mutations, the tumor microenvironment determines tumor metastatic phenotype.

This research has led to a new understanding of the impact of the tumor microenvironment heterogeneity upon proliferation, and more importantly, dissemination. In previous studies, certain of the inventors examined the role that tumor micro-environmental parameters (hypoxia, stromal and immune cells, extracellular matrix, stemness) have on breast cancer cell dissemination and dormancy in vivo, and at single cell resolution, using novel multiphoton imaging tools and intravital imaging techniques. This research highlights how high-resolution imaging can identify, localize, and quantify heterogeneity in the tumor microenvironment, in vivo, and reveal cell-cell interactions and mechanisms that cannot be observed using fixed tissue, i.e., tissue samples which have been cross-linked in paraformaldehyde (PFA) and then, stained for selected antibodies to allow for imaging by microscopy. A full understanding of this heterogeneity, both temporally and spatially, in the primary and secondary sites; how it supports tumor cell dissemination, dormancy and eventual further metastatic growth; and how it responds to therapeutic interventions, is crucial since it can reveal commonalities and differences that could lead to unique treatment approaches and therapies.

To accomplish this, experiments designed to identify, locate, and characterize the function of the cells contributing to this microenvironment need to be performed at widely varying temporal and spatial scales (from minutes to weeks and from sub-cellular to tissue wide) and at vastly different stages (initiation on to metastasis), in order to give a complete understanding of tumor progression. Unfortunately, this understanding has been delayed by significant limitations of approaches that are currently employed.

Conventional tools like 2D in vitro assays do not adequately reflect the topography encountered by cells in vivo. Even 3D in vitro assays which remove this restriction on topography, still lack the diversity and heterogeneity of environments present in the living organism (e.g. multiple host cell interactions, physiological extracellular matrix, connection to lymphatic and vascular circuits, etc.). Thus in vivo methods are essential; however quantitation of cell subsets in in vivo tissues is typically accomplished either by histology or FACS (Fluorescence Activated Cell Sorter) analysis. These methods are also limited as they can only be used in single time point, end-stage experiments, with FACS additionally disrupting the tissue spatial arrangement.

Identification of cell types can alternatively be accomplished by using genetically modified mouse models. Unfortunately, these models take months to years to develop and are not applicable to human tissues. Further, those experiments that are performed in living animals are typically limited to systemic applications of drugs, functional blocking antibodies, or inducible genetic alterations that are un-localized and create many off-target effects that can confound experimental results. Furthermore, analyses of these approaches again relies on end-stage assays of fixed tissues followed by histology or FACS.

What is needed is the ability to visualize, identify and manipulate specific cell types and their dynamics while they are resident in the living tissue at both the primary and various secondary sites.

Existing intravital windows facilitate repeated imaging in vivo but generally inhibit introduction of drugs or other fluids to adjacent target tissue after window installation. US published application 2014/0308207 discloses an on-chip microfluidic device (OMD) providing microscopic observation and creating gradients in the underlying tissue. However, the OMD employs constant one-way flow, generated by syringe pumps, to diffuse chemoattractant solution into tissue, and requires tubing and a housing structure for importing the solution from the external environment. Further, the OMD is constrained to release its chemoattractant solution through all of its outlets simultaneously and at one time.

A more compact, efficient, remotely controllable and versatile microfluidic intravital window is desirable.

BRIEF DESCRIPTION OF THE INVENTION

The current invention directly addresses and overcomes these limitations by providing a microfluidic intravital window that facilitates identifying and manipulating, simultaneously, subsets of cells in vivo. The present invention combines materials science and optical physics technologies with in vivo imaging and molecular biological techniques to not only observe, but actively manipulate, tumor microenvironments within a living animal, giving a similar level of control over experimental parameters to those that researchers have when working in vitro, and enabling researchers and other users to go beyond correlative studies and determine causative relationships.

The tumor microenvironment is a multi-faceted, complex milieu for study. Tumor analysis while within the context of its heterogeneous composition, especially with regard to the identity, location and function of cell types, may provide unique insights into some of the most difficult and important questions in cancer research. The present invention addresses this need, by providing a tool to analyze the tumor in vivo and in real time, with simultaneous remotely controlled release of preloaded factor(s), drug(s), biochemical(s), chemotactic agent(s) or other fluid(s) and imaging studies.

Further, the microfluidic intravital window of the present invention is compact, completely self-contained, remotely activated, dynamically controllable, efficient and versatile in application, and readily fabricated using soft lithography processes.

A microfluidic intravital window, according to the present invention, includes: an intravital imaging window adapted for implantation adjacent target tissue of a live animal; and a microfluidic fluid source and delivery system physically integrated into the window for controlled delivery of fluid to the target tissue via the window. The microfluidic fluid source and delivery system is self-contained and completely located within the intravital imaging window and includes at least one preloaded fluid reservoir, at least one fluid port in fluidic communication with both the at least one preloaded fluid reservoir and the target tissue, and at least one remotely activated fluid flow control device situated between the at least one preloaded fluid reservoir and the at least one fluid port, whereby simultaneous in vivo viewing and remotely controlled fluid delivery to the target tissue are facilitated.

Advantageously, the at least one remotely activated fluid flow control device may comprise at least one light activated fluid flow control device. The at least one light activated fluid flow control device may include a material having a shape that changes when irradiated with light. Preferably, the material has a shape that reversibly changes when alternately irradiated with visible light of different polarizations. In a preferred embodiment, the material may comprise an azobenzene polymer. Advantageously, the material may comprise multiple parallel, spaced apart, strips of azobenzene film extending along a long axis of the film.

The at least one light activated fluid flow control device may comprise at least one of a light activated, microfluidic: valve, pump, mixer, or dynamic fluid diverter.

The light activated microfluidic valve may include at least one of a light sensitive cantilever element or a light sensitive diaphragm element. Alternatively, the light activated microfluidic valve may include a surface or layer exhibiting a topography change when irradiated with light, e.g., a surface comprising a surface relief grating or grid with holographic light activated reversible surface patterning.

The light activated microfluidic pump may be unidirectional, and the microfluidic fluid delivery system may further include a one-way check valve upstream and/or downstream of the light activated microfluidic pump to prevent backfill.

Alternatively, the light activated microfluidic pump may comprise a reciprocal micro-pump with a light activated oscillating membrane, and may be adapted to deliver fluid to the target tissue and/or extract fluid from the target tissue.

The intravital imaging window may comprise a glass coverslip within a frame, with the frame adapted for attachment to skin of the live animal with an inner surface of the window situated adjacent the target tissue, and the microfluidic fluid source and delivery system may be completely located on the inner surface of the intravital imaging window.

The target tissue may comprise a tumor microenvironment, and the fluid may comprise a factor, drug or chemotactic agent.

The microfluidic fluid delivery system may comprises a cured PDMS structure sealed to the intravital imaging window.

The microfluidic intravital window may further include at least one microneedle extending from an inner surface of the intravital imaging window into the target tissue to help anchor the window to the target tissue.

The microfluidic intravital window may also comprise at least one hollow microneedle in fluid communication with the at least one fluid port and extending into the target tissue to deliver the fluid at a desired depth within the target tissue.

The at least one fluid reservoir of the microfluidic intravital window may include multiple reservoirs respectively preloaded with different fluids for simultaneous and/or sequential remotely controlled delivery of the different fluids to the target tissue. At least one light activated fluid flow control device may be situated downstream of each reservoir.

The at least one fluid port of the microfluidic intravital window may include multiple fluid ports adjacent different regions of the target tissue for simultaneous and/or sequential remotely controlled delivery of fluid(s) to the different regions of the target tissue.

In a further aspect, the microfluidic intravital window of the present invention may comprise: an intravital imaging window adapted for implantation with an inner surface of the intravital window adjacent target tissue of a live animal; and a microfluidic fluid source and delivery system physically integrated into the window for controlled delivery of fluid to the target tissue via the window. The microfluidic fluid source and delivery system is self-contained and completely located on the inner surface of the intravital imaging window and includes at least one preloaded fluid reservoir, at least one fluid port in fluidic communication with both the at least one preloaded fluid reservoir and the target tissue, and at least one light activated fluid flow control device situated between the at least one preloaded fluid reservoir and the at least one fluid port, whereby simultaneous in vivo viewing and light controlled fluid delivery to the target tissue are facilitated.

BRIEF DESCRIPTION OF THE DRAWING FIGURES

Figure 4:
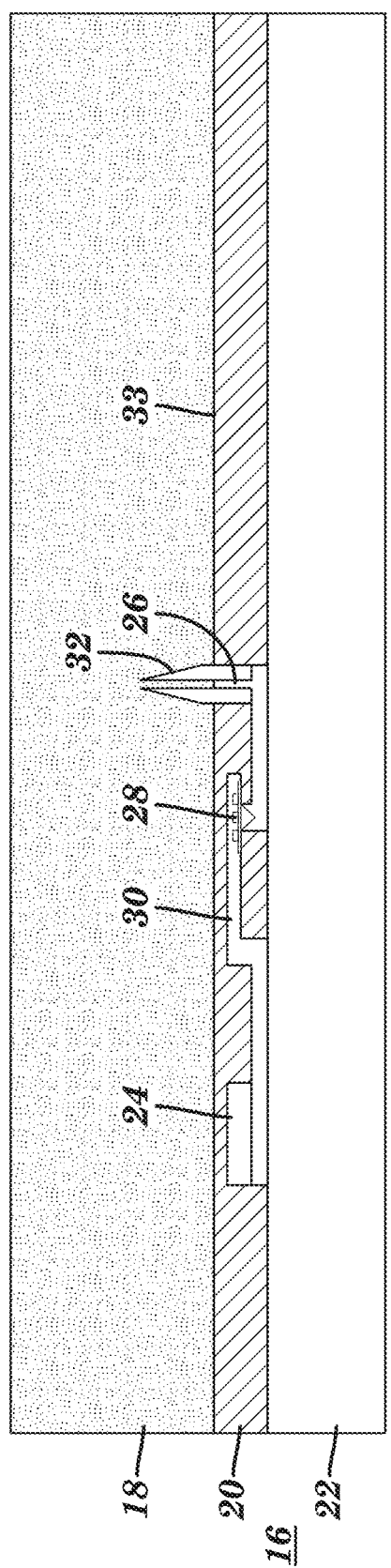
Figure 6:
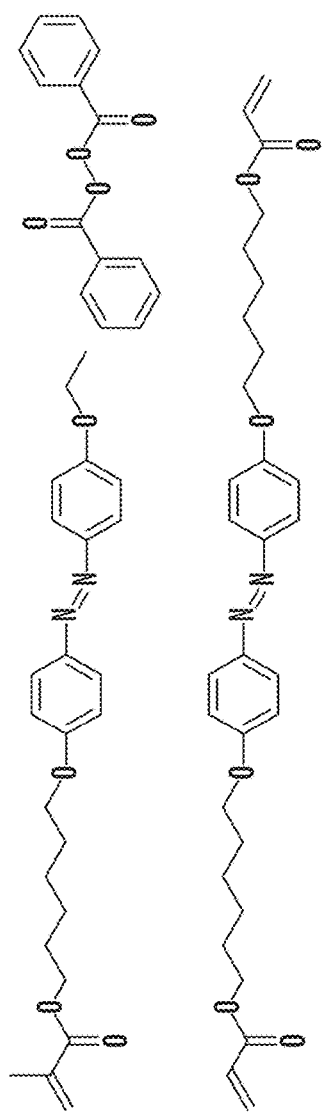
Figure 7:
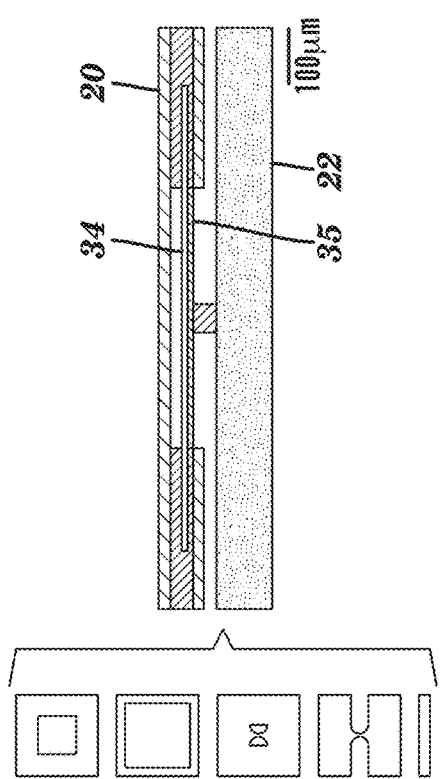
Figure 10A:
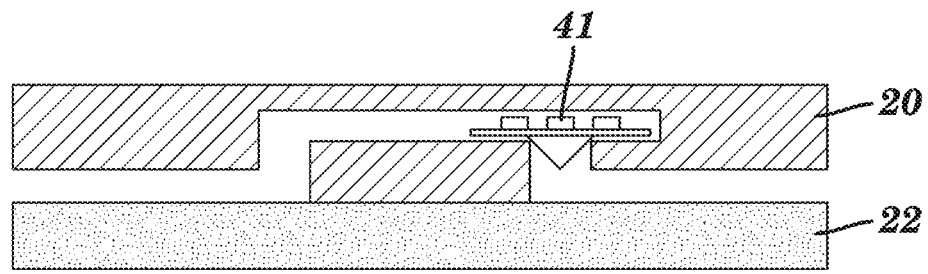
Figure 10B:
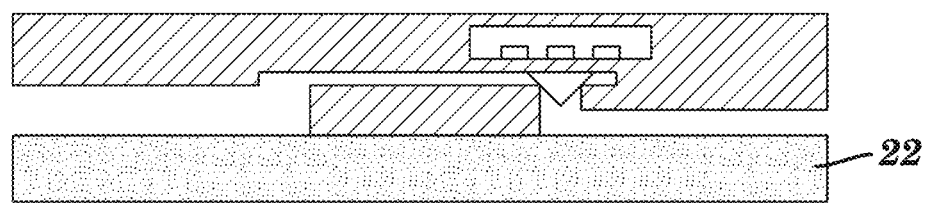
Figure 10C:
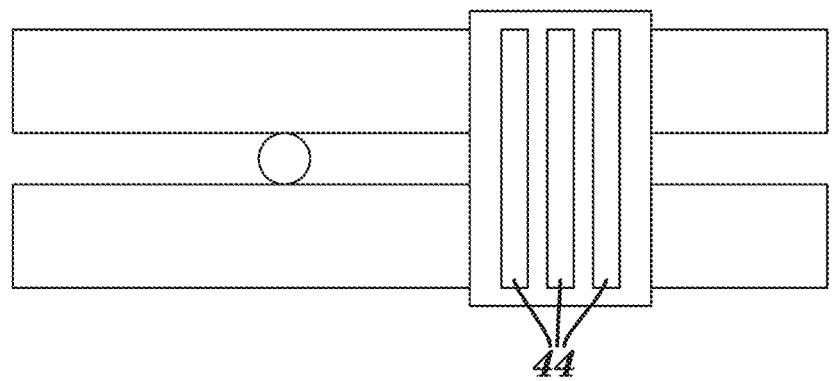
Figure 11B:
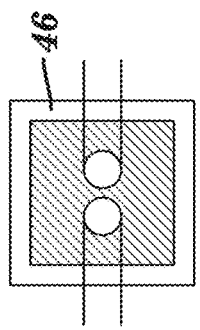
Figure 11C:
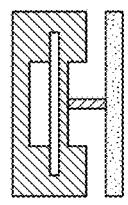
Figure 11D:
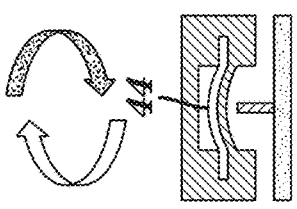
Figure 11A:
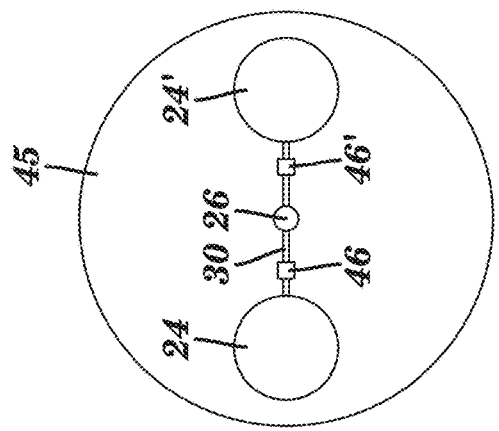
Figure 12:
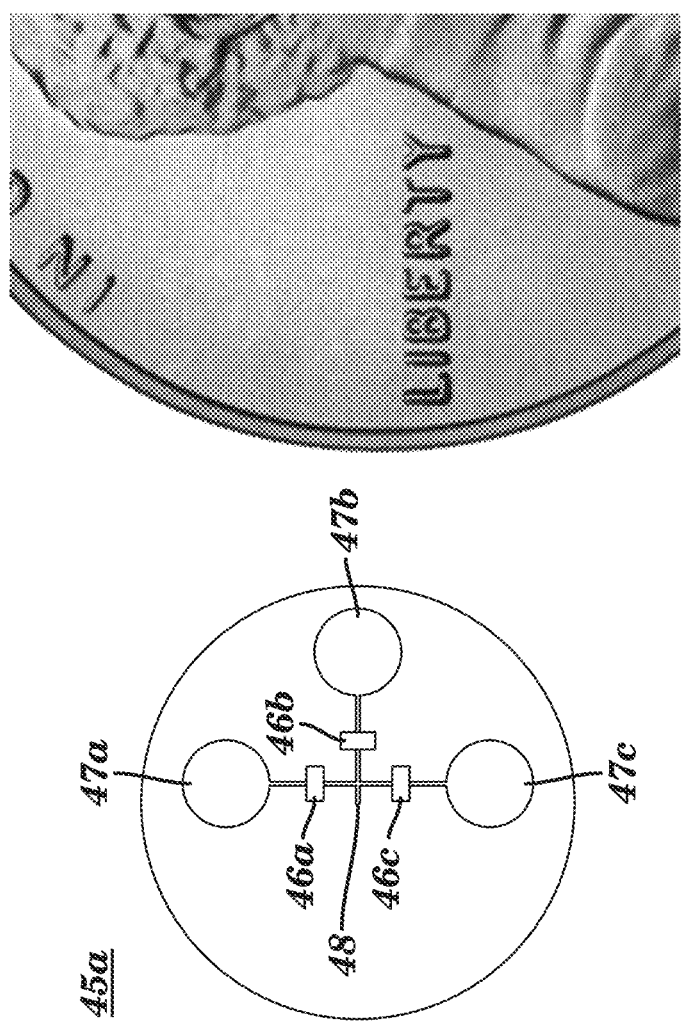
Figure 14A:
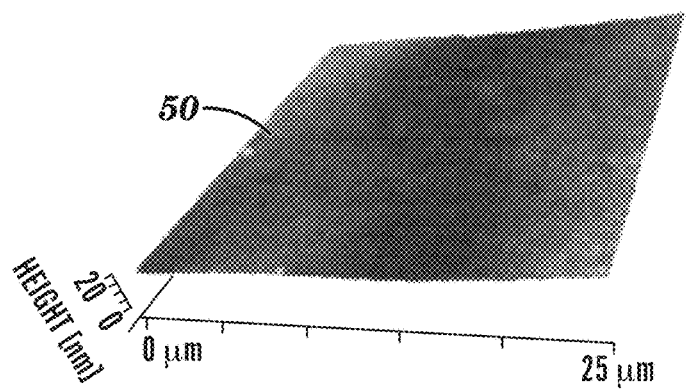
Figure 14B:
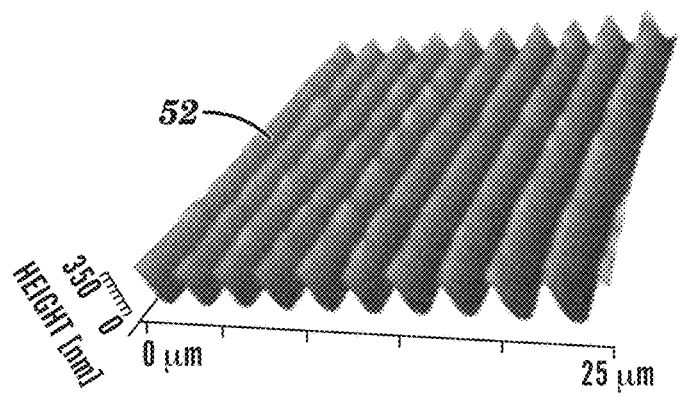
Figure 14C:
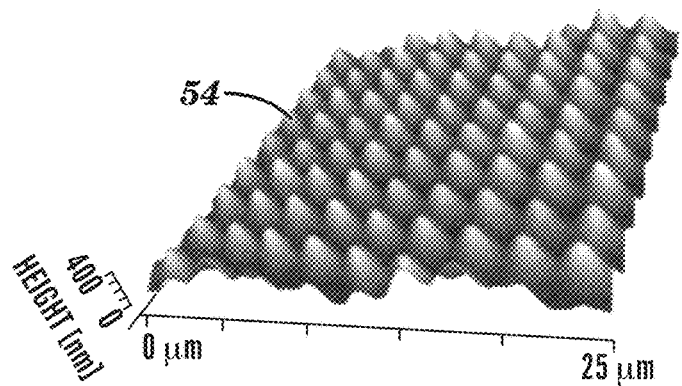
Figure 15:
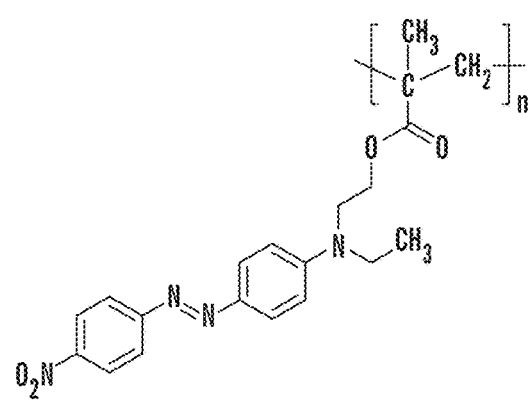
Figure 16A:
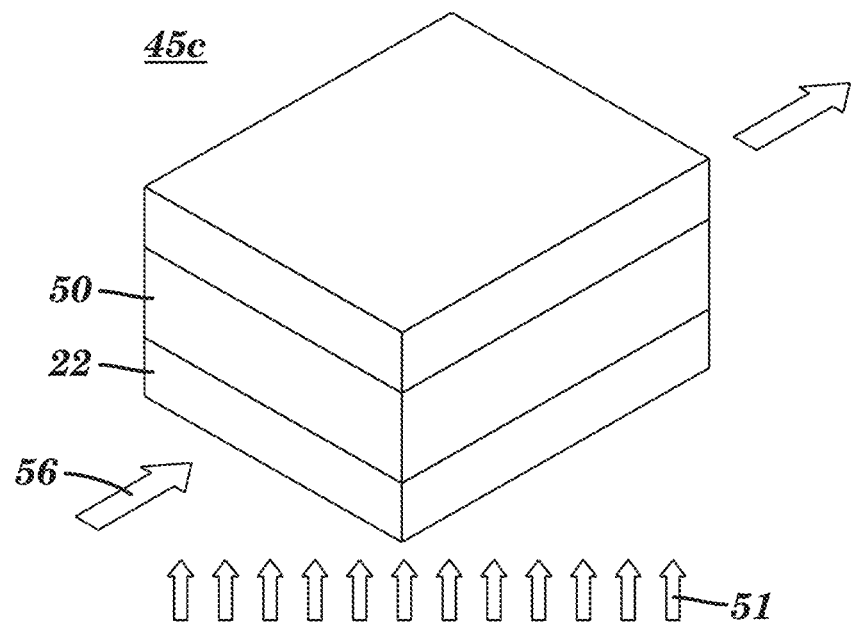
Figure 16B:
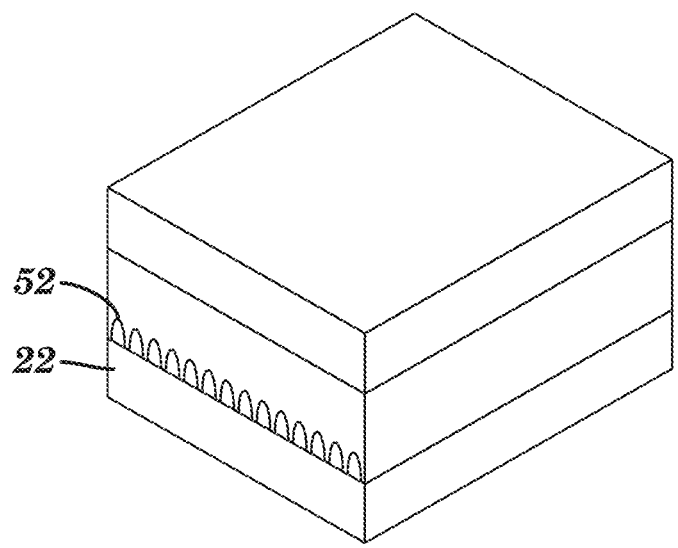
Figure 17:
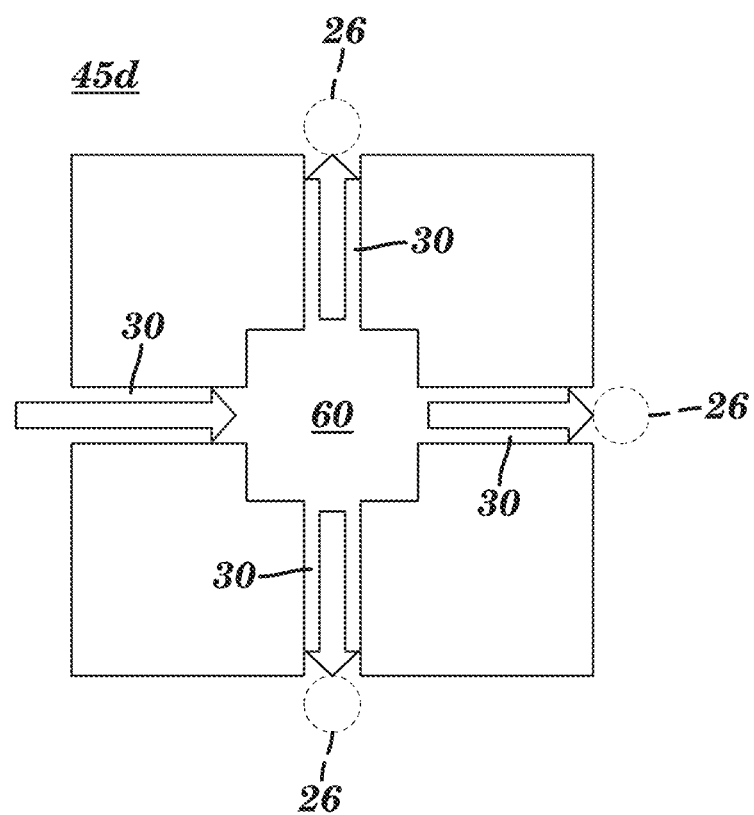
Figure 18A:
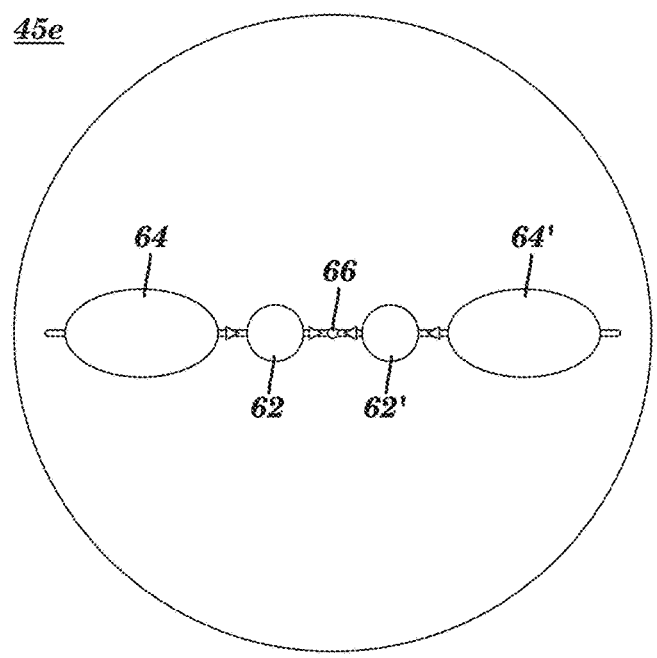
Figure 18B:
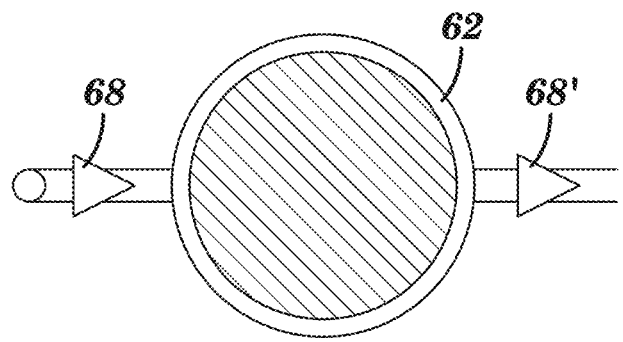
Figure 18C:
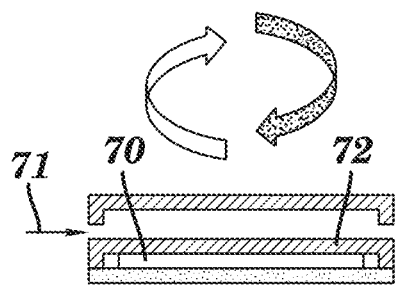
Figure 18D:
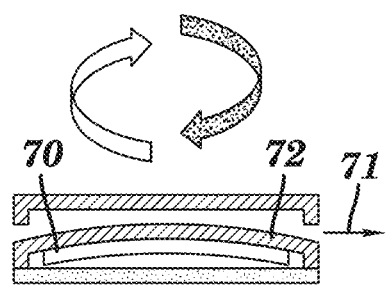

FIGS. 3A-3D schematically depict various installation sites of an intravital window in a mouse;

FIG. 4 is a sectional view from the side of one embodiment of the microfluidic intravital window of the present invention;

FIG. 5 depicts fabrication of a PDMS structure for inclusion in the microfluidic intravital window of the present invention;

FIG. 6 represents the chemical structure of azobenzene polymers useful in the light activated fluid flow control devices of the present invention;

FIG. 7 depicts the structure of a light activated fluid flow control device of the present invention;

FIGS. 8A, 8B and 8C depict a cantilever design of a light activated fluid flow valve, in side view with the valve closed, in side view with the valve open, and in top view, respectively;

FIGS. 9A, 9B and 9C depict a diaphragm design of a light activated fluid flow valve, in side view with the valve closed, in side view with the valve open, and in top view, respectively;

FIGS. 10A, 10B and 10C depict a sectional view from the side of a self-sealing light activated fluid flow valve, a sectional view from the side of an easy to assemble light activated fluid flow valve, and a top view, respectively;

FIG. 11A is a plan view of a passive microfluidic intravital window including two fluid reservoirs preloaded with different fluids, with a light activated fluid flow valve downstream of each reservoir, and a central fluid port; FIGS. 11B-11D depict, in sectional views, the reversible operation of the valve(s);

FIG. 12 depicts an embodiment with 3 preloaded fluid reservoirs and a light activated fluid flow valve downstream of each reservoir, adjacent a penny to illustrate scale;

FIG. 13 depicts an embodiment with 4 preloaded fluid reservoirs and a light activated fluid flow valve downstream of each reservoir, adjacent a penny to illustrate scale;

FIGS. 14A-14C illustrate surface topography changes of a light reversible azobenzene film surface or layer;

FIG. 15 represents a chemical structure of an azobenzene film suitable for use in the surface relief structures of FIGS. 14A-14C;

FIGS. 16A and 16B depict operation of a surface relief grating fluid flow valve;

FIG. 17 depicts a light activated fluid flow control device situated at a four-way intersection facilitating simultaneous and/or sequential controlled delivery of fluid to different regions of the target tissue; and FIG. 18A is a plan view of an active microfluidic intravital window having two preloaded fluid reservoirs with a light activated microfluidic pump downstream of each reservoir; FIGS. 18B-18D depict, in sectional views, the light activated operation of the pump(s).

DETAILED DESCRIPTION

Figure 1:
FIG. 1 depicts a known intravital window installed in a mouse.

FIG. 1 illustrates a conventional intravital window installed in a living mouse. Typical dimensions and a configuration of the intravital window 10 are depicted in FIGS. 2A and 2B, respectively.

Figure 2B:
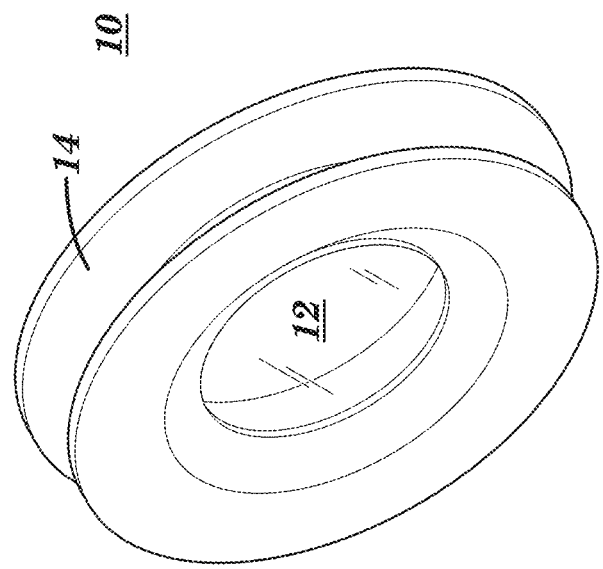
FIGS. 2A and 2B depict dimensions and a configuration, respectively, of a conventional intravital window.
Figure 2A:
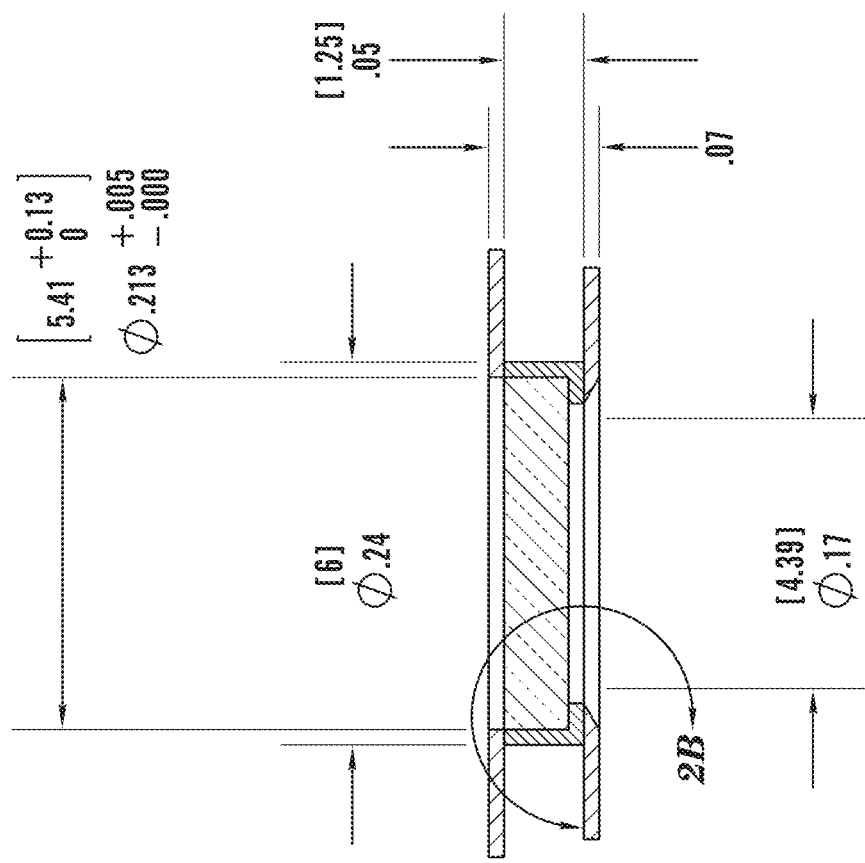

The intravital window 10 may comprise a glass coverslip 12 mounted within a metal frame 14 as most clearly illustrated in FIG. 2B.

The conventional intravital window is installed by suturing or otherwise attaching the metal frame to skin of the live animal adjacent target tissue, and facilitates repeated in vivo imaging. The window may be secured at various locations in the mouse, or other living animal, to provide, for example, a cranial window, a dorsal skinfold chamber, a mammary imaging window, or an abdominal imaging window, as schematically illustrated in FIGS. 3A-3D, respectively. Although a conventional intravital window facilitates repeated in vivo imaging, it inhibits introduction of drugs or other fluids to the adjacent target tissue after window installation. The microfluidic intravital window of the present invention overcomes this limitation in a particularly advantageous manner.

FIG. 4 depicts an embodiment of a microfluidic intravital window 16, of the present invention, installed adjacent target (e.g., tumor) tissue 18. The microfluidic intravital window 16 includes a microfluidic fluid source and delivery system 20 physically integrated with an intravital imaging window 22. The intravital imaging window 22 may be of conventional construction comprising, for example, a glass coverslip within a frame, with the frame adapted for attachment to skin of the live animal.

The microfluidic fluid source and delivery system 20 is self-contained and completely located within the microfluidic intravital imaging window 16, and includes at least one preloaded fluid reservoir 24, at least one fluid port 26 in fluidic communication with both the at least one preloaded fluid reservoir 24 and the target tissue 18, and at least one remotely activated fluid flow control device 28 situated between the at least one preloaded fluid reservoir 24 and the at least one fluid port 26. Fluid flow channels 30 interconnect the various components of the microfluidic fluid source and delivery system.

Optionally, at least one microneedle 32 may extend from an inner surface 33 of the microfluidic intravital imaging window 16 into the target tissue 18 to help anchor the window in the target tissue. Advantageously, at least one hollow microneedle 32 may be in fluid communication with the at least one fluid port 26 for delivering fluid at a desired or optimal depth into the target tissue, for example, at an ideal imaging depth of 100-150 µm of a multiphoton microscope.

The microfluidic intravital window 16 may utilize soft-lithography techniques for fabrication of the desired microfluidic features. As illustrated in steps A-E of FIG. 5, master molds may be fabricated in a cleanroom by patterning SU-8 onto silicon wafers. The molds may then be coated in a silanizing agent and uncured polydimethylsiloxane (PDMS) poured into the mold (step F). This construct may be left in an oven overnight. Cured PDMS may be peeled off of the wafer (step G), retaining the features of the master mold. This PDMS structure may represent the main component of the microfluidic fluid source and delivery system 20. The PDMS structure may be loaded with various fluids or factors and sealed irreversibly to a glass coverslip 22 of the same dimension (step H). Completed windows may be mounted into a metal frame that is stitched into the mouse, or other living animal, for installation.

A photo-reactive polymer may be used to remotely operate the microfluidics of the microfluidic intravital window. This approach allows complete control of the microfluidic fluid delivery system without any resultant temperature or pH change or other disturbance of the target tissue.

Azobenzene-based polymer films, as represented in FIG. 6, may be synthesized and polymerized so that they predictably bend in response to visible light, e.g., 488 nm wavelength light, of a first polarization. Furthermore, the polymer film bends back/reverts to its original shape in the presence of visible light, e.g. 488 nm light, of a second, different polarization (e.g., 90° rotated from the first polarization) making the process indefinitely reversible. Moreover, no by-products are released in the process.

A microfluidic fluid delivery system utilizing photo-actuation as the driving mechanism allows for release of drugs, factors, biochemicals, chemotactic agents or other fluids from the window in both passive and active modes. Passive microfluidic intravital windows contain off/on light activated fluid flow valves to restrict and allow access to each device outlet. Upon light activation, the valves are switched to "ON", causing diffuse flow through the device.

Active microfluidic intravital windows may contain reciprocal diaphragm micro-pumps, which convert oscillating pressure sources into one-way flow. Such pressure sources may be generated by an azobenzene membrane, which is exposed to 488 nm wavelength light of sequentially 90° rotated polarization, causing oscillation. Each oscillation pushes a fixed volume of fluid out of the device outlet(s).

Ideal utilization of the passive and/or active microfluidic intravital windows of the present invention is in conjunction with two-photon excitation microscopy. The window may be preloaded with drugs, factors, biochemicals, chemotactic agents or other fluids and installed into the skin of a mouse or other living animal. The inside face or inner surface of the window may make direct contact with the surface of the tumor, and imaging may begin in the region immediately around the window outlet. After some amount of time, the window is activated and the drugs, factors, biochemical, chemotactic agents or other fluids released into the tumor microenvironment. The subsequent cellular response may be imaged with subcellular resolution for many days. Multiple fluid reservoirs can be utilized for sequential drug release to study treatment programs in vivo. Similarly, multiple outlet ports may be utilized for simultaneous or sequential fluid release to different regions of the target (tumor) tissue.

The light activated fluid flow control device of this invention may utilize a film of the polymer azobenzene, which, when irradiated with visible light, e.g., 488 nm wavelength light, polarized parallel to a long axis of the azobenzene film, undergoes a conformational change. This phenomenon, amplified along a film of the polymer, yields macroscopic bending behavior. Furthermore, irradiation with visible light, e.g. 488 nm wavelength light, polarized perpendicularly to the long axis of the azobenzene film, fully reverses the bending effect, allowing for repeated cycling of photo-actuation. The photo-actuation process induces no temperature change, no pH change, no deleterious effect on the target tissue, and is clean and efficient.

Light activated azobenzene polymer films may be formed through in situ thermal polymerization. A mixture of azobenzene monomer, azobenzene crosslinker, and thermal initiator (e.g. benzoyl peroxide) may be heated to a molten phase. The mixture may then be "sandwiched" between two glass slides that may be coated with an alignment layer such as Elvamide® nylon multipolymer resin, available from E. I. du Pont de Nemours and Company, or the like, and heated to activate polymerization. Peripheral spacers may be located between the two glass slides to ensure uniform film thickness. The slides may then be removed and the free-standing film cut into desired sizes.

PDMS valves housing the azobenzene films may be micro-fabricated using soft lithography and sealed through oxygen plasma treatment.

The microfluidic intravital window of the present invention may contain a single or multiple reservoirs. These reservoirs may contain tuned hydrogel, or similar material, for optimal time release of loaded factors. The primary structures of the microfluidic intravital window may be fabricated and assembled using soft lithography methods, as described above. Single reservoir devices may be assembled from layers of PDMS sealed to a glass coverslip, as depicted in FIG. 7. With the "membrane sandwich" method, completed layers may be sealed together after surface activation by oxygen plasma to form microfluidic components and micro-channels.

Multiple-reservoir microfluidic intravital windows allow the preloading and release of several factors in vivo. These devices may be used for temporal as well as spatial drug release. Spatial-release devices may have multiple outlets throughout the device, allowing simultaneous comparison of several regions of target (tumor) tissue. Temporal-release devices may be loaded with hydrogels of varying composition to affect the rate of release of each factor.

In FIG. 7, the PDMS structure 20 is fabricated on a surface of the glass coverslip 22 and includes a light activated azobenzene film 34, mounted upon a PDMS support member 35, acting as a diaphragm, to open and close the valve. The various layers of the microfluidic intravital window are shown on the left side of FIG. 7.

In FIGS. 8A-8C, a light activated fluid flow valve 37 of cantilever design is illustrated. The cantilever arm 36 includes a layer (or strips, as depicted in the top view of FIG. 8C) 38 of azobenzene film and a stopper element 40 at its remote end. As shown in FIG. 8B, irradiation of the layer (or strips) 38 of azobenzene film, on the cantilever arm 36, with light of a selected polarization, causes the cantilever arm to bend thereby opening the valve. Irradiation of the layer (or strips) 38 of azobenzene film, on the cantilever arm 36, with light of a different select polarization causes the arm 36 to revert to its closed position as illustrated in FIG. 8A. This reversible macroscopic bending motion may facilitate remotely controlled fluid flow through the valve 37. Since azobenzene films bend with respect to their long axis, the use of multiple parallel strips 38 of the film, as depicted in FIG. 8C, may advantageously produce more bending motion than a single wider film.

FIGS. 9A-9C illustrate a light activated fluid flow valve 41 of diaphragm design. In this embodiment, a diaphragm member 42 of PDMS bears an azobenzene film layer (or strips, as depicted in the top view of FIG. 9C) 44 on one side, and a stopper element 40 on an opposite side. Irradiation of the azobenzene film layer (or strips) 44, on the diaphragm member 42, with light of specified different polarizations will cause the diaphragm element to bend and thereby open the valve as illustrated in FIG. 9B or revert to its original planar position to close the valve, respectively, as illustrated in FIG. 9A.

As illustrated in FIGS. 10A-10C, a valve 41 of the diaphragm design may be included in the PDMS structure 20 as a self-sealing element (FIG. 10A) or an easy to assemble valve element (FIG. 10B). FIG. 10C provides a top plan view of this construction.

FIG. 11A presents a plan view of a passive microfluidic intravital window 45 having two separate fluid reservoirs 24, 24' for different factors, a respective light activated fluid flow valve 46, 46' downstream of each reservoir, a central outlet port 26, and fluid flow channels 30 interconnecting these components. The passive microfluidic intravital window 45 may, for example, have a diameter of 8 mm, and a device thickness of 150-200 µm.

The sectional views of FIGS. 11B-11D illustrate the operation of valves 46 and 46'. As depicted in FIG. 11D, the azobenzene film 34 causes the diaphragm element of the valve to mechanically deform when irradiated with 488 nm light of a first polarization parallel to a long axis of the film. The diaphragm element returns to its initial state, as shown in FIG. 11C, when irradiated with 488 nm light of a second polarization perpendicular to the long axis of the film.

FIGS. 12 and 13 illustrate different embodiments of the microfluidic intravital window 45a, 45b of the present invention with multiple reservoirs 47a . . . 47d, associated light activated valves 46a . . . 46d, and at least one fluid port 48. In each of these illustrations, a penny is depicted to show relative scale of the microfluidic intravital window.

In accordance with the principles of the present invention, the number, layout, configuration, shape, size, dimensions, locations and contents of the fluid reservoirs may vary. Similarly, the number, location and construction of the light activated fluid flow control elements and the fluid ports may vary. FIG. 12 illustrates a three reservoir, three valve arrangement, while FIG. 4 depicts a four reservoir, four valve arrangement. The same or different fluids may be preloaded in the different reservoirs, and the light activated fluid flow control devices may be selectively activated for sequential or simultaneous release of the fluid(s).

An alternative light activated fluid flow control device 45c is illustrated in FIGS. 14A-14C, 15, 16A and 16B. In this embodiment, holographic light patterning 51 causes reversible surface topography changes in a commercially available azobenzene film layer 50. The holographic patterning may produce a surface relief grating 52 as illustrated in FIG. 14B, or a surface relief grid 54 as illustrated in FIG. 14C, or other 3 dimensional shape. The light activated reversible surface patterning may be used to form a fluid flow valve 45c.

A chemical structure of an azobenzene film suitable for use in the reversible, light activated, surface relief patterning of FIGS. 14A-14C, and operation of a surface relief grating fluid flow valve 45c are illustrated in FIGS. 15, and 16A-16B, respectively. FIG. 16B depicts a holographically induced topological surface change in an azobenzene film layer 50 resulting in formation of fluidic channels in fluid flow direction 56.

FIG. 17 schematically illustrates another configuration of a microfluidic intravital window 45d according to the present invention. In this embodiment, a light activated fluid flow control device 60 is situated at a four-way intersection of micro-channels 30 to selectively control fluid flow out of multiple spatially distributed fluid outlet ports 26 to distribute the fluid to different regions of the target tissue.

FIG. 18A presents a plan view of an active microfluidic intravital window 45e employing light activated, fluid flow control micro-pumps 62, 62'. Each micro-pump may be situated between a respective fluid reservoir 64, 64' and a fluid outlet port 66. Advantageously, a one-way check valve 68, 68' may be situated upstream and downstream respectively, of each micro-pump 62, 62', as shown in FIG. 18B, to prevent backfill. As illustrated in FIGS. 18C and 18D, light of different polarizations (e.g. parallel versus perpendicular, at 488 nm) may be employed to alternately bend and relax (revert to its original shape) an azobenzene film layer 70, of diaphragm design, of the micro-pump. For example, light polarized parallel to a long axis of the azobenzene film yields bending toward the light source; perpendicularly-polarized light yields unbending of the azobenzene film.

Micro-pumps 62, 62' may comprise reciprocal micro-pumps having an oscillating membrane 72. When situated between a pair of similarly oriented one-way valves 68, 68', the reciprocal micro-pumps facilitate pressure-driven release of factors or other fluids from the associated fluid reservoir(s). As the membrane 72 deflects (FIG. 18D), a pressure gradient is formed, causing flow in the direction 71 of the one-way valves. Return of the membrane to its original position (FIG. 18C) then causes negative pressure to draw in more fluid from the inlet channel connected to the fluid reservoir. The oscillating membrane 72 bears the azobenzene film layer 70 which can be activated to bend and relax by alternating polarizations of incident light.

Other active microfluidic components for fluid flow control, such as mixers, e.g. utilizing a "herringbone" structure, may be employed for mixing fluids before they reach an outlet port. Likewise, multiple similar and/or different fluidic flow control devices may be combined to perform sophisticated microfluidic functions within the microfluidic intravital window.

Although various embodiments have been described and depicted herein, the microfluidic intravital window of the present invention may assume other configurations. For example, the components of the self-contained microfluidic fluid source and delivery system may vary as well as their material, construction, number and location within the intravital window. The size, length, depth, cross-section, path and the like of the channels interconnecting the components may also vary. The wavelengths, polarizations and/or other characteristics of the activating light may also vary. The overall size, shape and composition of the window itself may also vary from that shown herein.

The light activated microfluidic intravital window of the present invention permits real time imaging of a preserved microenvironment while simultaneously, controllably affecting a tumor or other target tissue with spatially and/or temporally released factors or other fluids, in vivo. As such, the microfluidic intravital window of the present invention is a critical tool for cancer research and other biological, in vivo studies.

What is claimed is:

1. A microfluidic intravital window, comprising:
an intravital imaging window adapted for implantation adjacent target tissue of a live animal; and
a microfluidic fluid source and delivery system physically integrated into the window for controlled delivery of fluid to the target tissue via the window, wherein the microfluidic fluid source and delivery system is self-contained and completely located within the intravital imaging window and includes at least one preloaded fluid reservoir, at least one fluid port in fluidic communication with both the at least one preloaded fluid reservoir and the target tissue, and at least one remotely activated fluid flow control device situated between the at least one preloaded fluid reservoir and the at least one fluid port, whereby simultaneous in vivo viewing and remotely controlled fluid delivery to the target tissue are facilitated.

2. The microfluidic intravital window of claim 1, wherein the at least one remotely activated fluid flow control device comprises at least one light activated fluid flow control device.

3. The microfluidic intravital window of claim 2, wherein the at least one light activated fluid flow control device includes a material having a shape that changes when irradiated with light.

4. The microfluidic intravital window of claim 3, wherein the material has a shape that reversibly changes when alternately irradiated with light of different polarizations.

5. The microfluidic intravital window of claim 4, wherein the material comprises an azobenzene polymer.

6. The microfluidic intravital window of claim 2, wherein the at least one light activated fluid flow control device comprises at least one of a light activated, microfluidic: valve, pump, mixer, or dynamic fluid diverter.

7. The microfluidic intravital window of claim 6, wherein the light activated microfluidic valve includes a surface exhibiting a topography change when irradiated with light.

8. The microfluidic intravital window of claim 7, wherein the surface comprises a surface relief grating or a surface relief grid, with holographic light activated reversible surface patterning.

9. The microfluidic intravital window of claim 6, wherein the light activated microfluidic pump is unidirectional, and the microfluidic fluid delivery system further includes a one-way check valve upstream and/or downstream of the light activated microfluidic pump to prevent backfill.

10. The microfluidic intravital window of claim 6, wherein the light activated microfluidic pump comprises a reciprocal micro-pump with a light activated oscillating membrane, and is adapted to deliver fluid to the target tissue and/or extract fluid from the target tissue.

11. The microfluidic intravital window of claim 1, wherein the intravital imaging window comprises a glass coverslip within a frame, and the frame is adapted for attachment to skin of the live animal with an inner surface of the window situated adjacent the target tissue, and the microfluidic fluid source and delivery system is completely located on the inner surface of the intravital imaging window.

12. The microfluidic intravital window of claim 11, wherein the target tissue comprises a tumor microenvironment, and the fluid comprises a factor, drug or chemotactic agent.

13. The microfluidic intravital window of claim 1, wherein the microfluidic fluid source and delivery system comprises a cured PDMS structure sealed to the intravital imaging window.

14. The microfluidic intravital window of claim 1, further comprising at least one microneedle extending from an inner surface of the intravital imaging window into the target tissue to help anchor the window to the target tissue.

15. The microfluidic intravital window of claim 1, further comprising at least one hollow microneedle in fluid communication with the at least one fluid port and extending into the target tissue to deliver the fluid at a desired depth within the target tissue.

16. The microfluidic intravital window of claim 1, wherein the at least one fluid reservoir comprises multiple reservoirs respectively preloaded with different fluids for simultaneous and/or sequential remotely controlled delivery of the different fluids to the target tissue.

17. The microfluidic intravital window of claim 16, wherein the at least one fluid port comprises multiple fluid ports adjacent different regions of the target tissue for simultaneous and/or sequential remotely controlled delivery of the different fluids to the different regions of the target tissue.

18. The microfluidic intravital window of claim 16, wherein the at least one remotely activated fluid flow control device comprises a light activated fluid flow control device downstream of each reservoir.

19. The microfluidic intravital window of claim 4, wherein the material comprises multiple parallel, spaced apart, strips of azobenzene film extending along a long axis of the film.

20. The microfluidic intravital window of claim 6, wherein the light activated microfluidic valve includes at least one of a light sensitive cantilever element or a light sensitive diaphragm element.

21. A microfluidic intravital window, comprising:
an intravital imaging window adapted for implantation with an inner surface of the intravital window adjacent target tissue of a live animal; and
a microfluidic fluid source and delivery system physically integrated with the window for controlled delivery of fluid to the target tissue via the window, wherein the microfluidic fluid source and delivery system is self-contained and completely located on the inner surface of the intravital imaging window and includes at least one preloaded fluid reservoir, at least one fluid port in fluidic communication with both the at least one preloaded fluid reservoir and the target tissue, and at least one light activated fluid flow control device situated between the at least one preloaded fluid reservoir and the at least one fluid port, whereby simultaneous in vivo viewing and light controlled fluid delivery to the target tissue are facilitated.

* * * * *